United States Patent
Hu et al.

(10) Patent No.: US 8,013,158 B2
(45) Date of Patent: Sep. 6, 2011

(54) CRYSTALLINE FORMS OF TOPOTECAN HYDROCHLORIDE AND PROCESSES FOR MAKING THE SAME

(75) Inventors: Tsung-Cheng Hu, Yongjing Township, Changhua County (TW); Shu-Ping Chen, Kaohsiung (TW); Piin-Jye Harn, Tainan (TW); Chia-Lin Charlene Shieh, Kaohsiung (TW)

(73) Assignee: Scinopharm Taiwan Ltd., Tainan County (TW)

( * ) Notice: Subject to any disclaimer, the term of this patent is extended or adjusted under 35 U.S.C. 154(b) by 763 days.

(21) Appl. No.: 12/082,907

(22) Filed: Apr. 14, 2008

(65) Prior Publication Data
US 2008/0269493 A1 Oct. 30, 2008

Related U.S. Application Data (60) Provisional application No. 60/925,280, filed on Apr. 19, 2007.

(51) Int. Cl.
*C07D 491/22* (2006.01)
*C07D 491/147* (2006.01)

(52) U.S. Cl. .......................................... 546/48; 546/47

(58) Field of Classification Search .................... 546/48, 546/47
See application file for complete search history.

(56) References Cited

U.S. PATENT DOCUMENTS

| 5,004,758 | A | 4/1991 | Boehm et al. | |
| 7,547,785 | B2 * | 6/2009 | Palle et al. | 546/48 |
| 2007/0105885 | A1 | 5/2007 | Pathi et al. | |
| 2007/0149783 | A1 | 6/2007 | Palle et al. | |

FOREIGN PATENT DOCUMENTS

WO  WO/2005/046608  5/2005

OTHER PUBLICATIONS

Chen et al., Studies on the polymorph of topotecan hydrochloride and its stability, In: Zhongguo Shenghua Yaowu Zazhi, 2005, 26(5), p. 279-281.

Vogt et al., A study of variable hydration states in topotecan hydrochloride In: Journal of Pharmaceutical and Biomedical Analysis, 2006, 40(5), p. 1080-1088.

* cited by examiner

*Primary Examiner* — Charanjit Aulakh
(74) *Attorney, Agent, or Firm* — Cozen O'Connor (57) ABSTRACT

Novel crystalline forms of topotecan hydrochloride and processes of making the same are disclosed.

13 Claims, 11 Drawing Sheets

CRYSTALLINE FORMS OF TOPOTECAN HYDROCHLORIDE AND PROCESSES FOR MAKING THE SAME

RELATED APPLICATIONS

This application claims priority from U.S. Provisional Patent Application Ser. No. 60/925,280 which was filed on Apr. 19, 2007. The entire content of U.S. Provisional Patent Application Ser. No. 60/925,280 is incorporated herein by reference.

BACKGROUND OF THE INVENTION

1. Field of the Invention

The present application relates to crystalline forms of topotecan hydrochloride and processes for making the same.

2. Description of the Related Art

Topotecan hydrochloride is (10-[(dimethyl amino)methyl]-4-ethyl-4,9-dihydroxy-1H-pyrano[3',4':6,7]indolizino [1,2-b]quinol-ine-3,14(4H,12H)dione hydrochloride) a compound of formula (I)

U.S. Pat. No. 5,004,758 discloses water soluble camptothecin analogs, which includes topotecan (9-dimethylamino methyl-10-hydroxy camptothecin), preferably (S)-topotecan and its hydrochloride salt.

Figure 1:
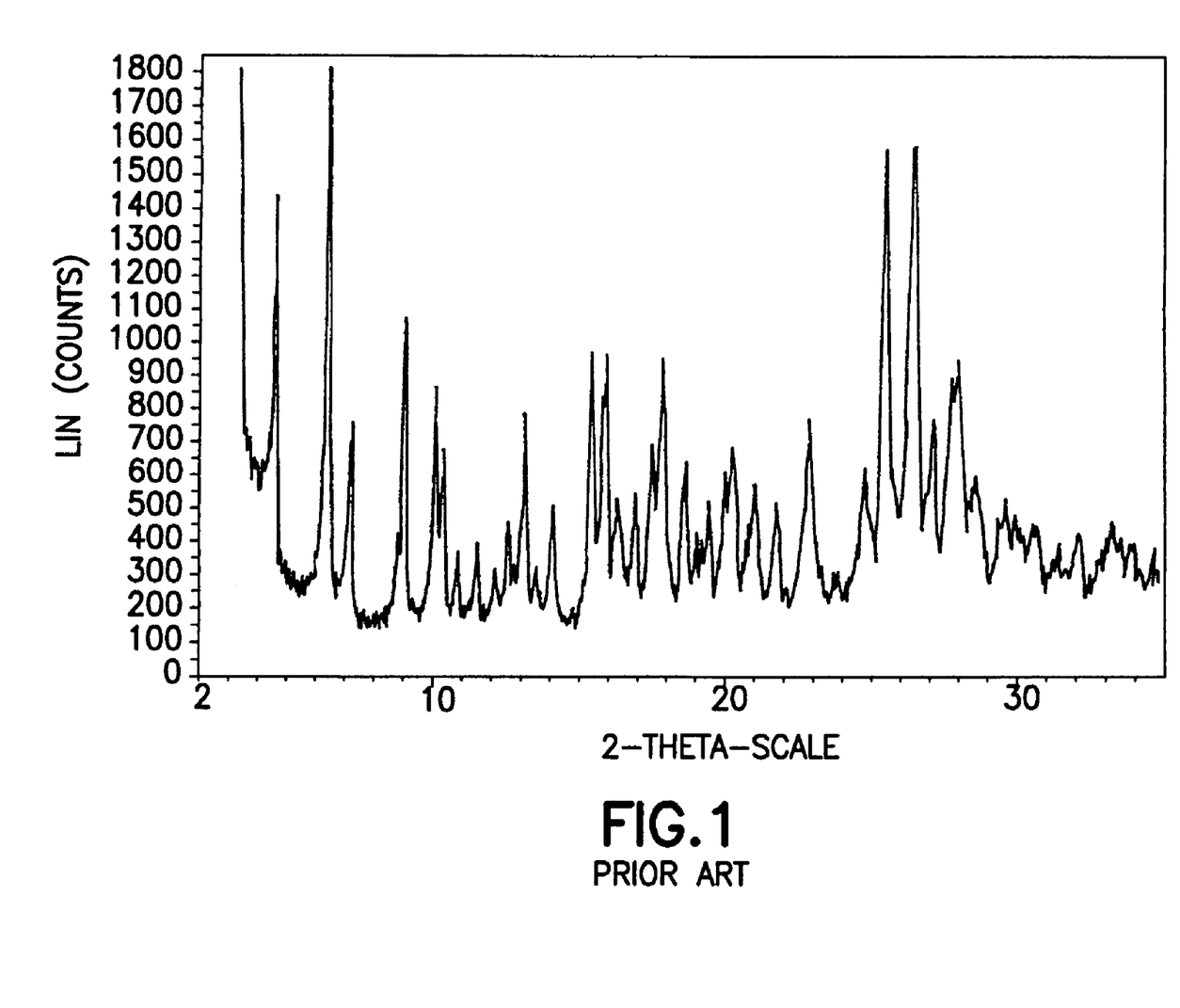
FIG. 1 is a characteristic powder X-ray diffraction pattern of Form A (WO2005/046608).
Figure 2:
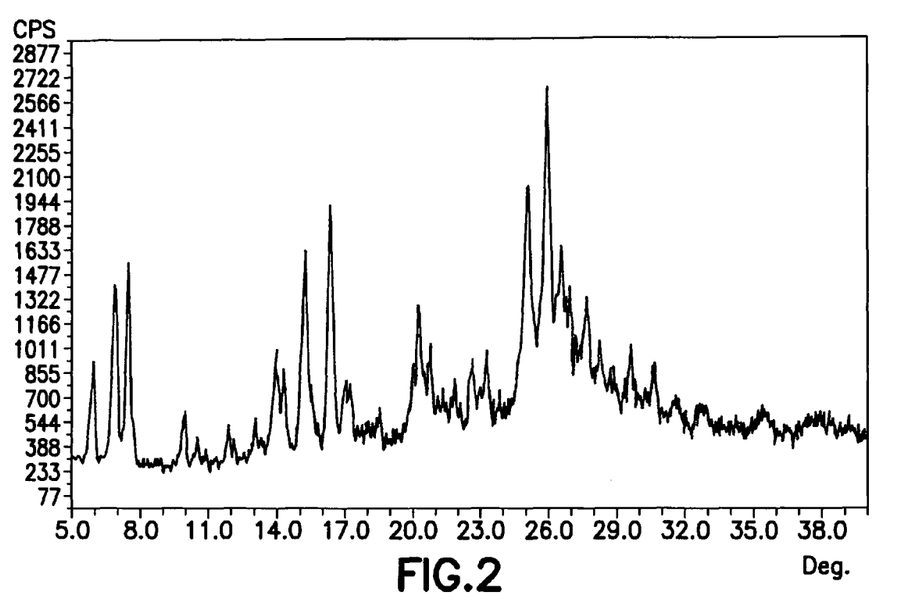
FIG. 2 is a characteristic powder X-ray diffraction pattern of Form C.
Figure 3:
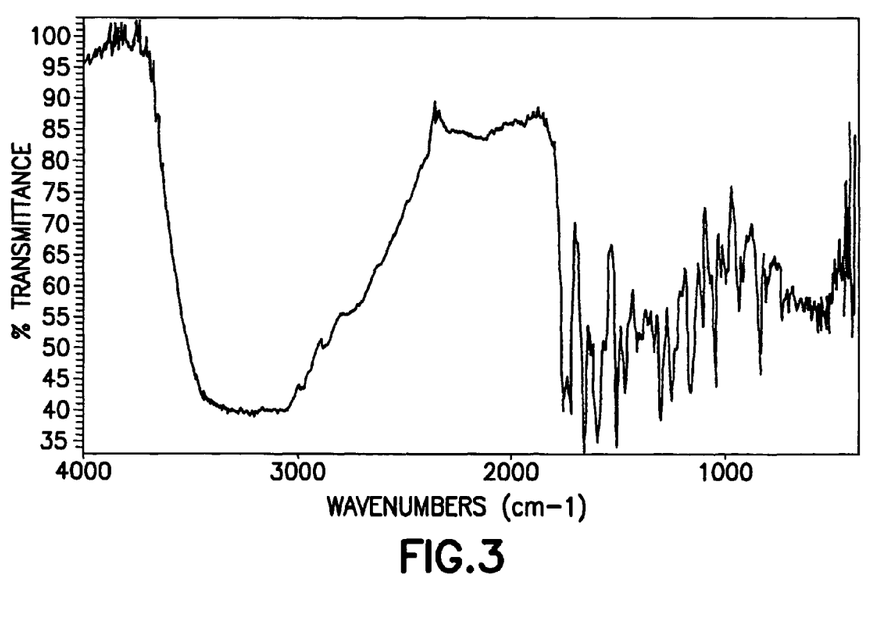
FIG. 3 is an infrared diffuse reflectance pattern of Form C.

PCT Application No. WO2005/046608 discloses a crystalline form of topotecan monohydrochloride pentahydrate with an X-ray diffraction pattern depicted in FIG. 1 therein. For the purpose of the present disclosure, this crystalline form is designated Form A.

SUMMARY OF THE INVENTION

The present invention relates to novel crystalline forms of topotecan hydrochloride that have been produced using a variety of crystallization processes. These crystalline forms are designated Forms B, C, D, E, F, G, H, I, J, and K.

The crystalline forms are characterized by their X-ray powder diffraction patterns and their IR spectra.

According to one aspect of the invention, there is provided a crystalline Form B of topotecan hydrochloride having an XRPD pattern with characteristic peaks at 6.1, 8.1, 23.4, 25.5 and 26.3° 2θ (±0.2°).

According to another aspect of the invention, there is provided a crystalline Form C of topotecan hydrochloride having an XRPD pattern with characteristic peaks at 6.9, 7.5, 15.1, 16.3, 25.1, and 26.0° 2θ (±0.2°). Preferably, crystalline Form C of topotecan hydrochloride has characteristic FT-IR peaks at 1754, 1723, 1658, 1597, and 1508 cm$^{-1}$.

According to further aspect of the invention, there is provided a crystalline Form D of topotecan hydrochloride having an XRPD pattern with characteristic peaks at 5.9, 13.9, 22.6, 23.2, and 26.5° 2θ (±0.2°). Preferably, crystalline Form D of topotecan hydrochloride has characteristic FT-IR peaks at 1742, 1654, 1586, 1510, and 1467 cm$^{-1}$.

According to yet another aspect of the invention, there is provided a crystalline Form E of topotecan hydrochloride having an XRPD pattern with characteristic peaks at 14.0, 18.8, 22.5, 25.4, and 25.7° 2θ (±0.2°). Preferably, crystalline Form E of topotecan hydrochloride has characteristic FT-IR peaks at 1752, 1649, 1584, 1567, and 1513 cm$^{-1}$.

According to further aspect of the invention, there is provided a crystalline Form F of topotecan hydrochloride having an XRPD pattern with characteristic peaks at 6.7, 12.4, 24.9, 25.4, 25.7, and 26.8° 2θ (±0.2°). Preferably, crystalline Form F of topotecan hydrochloride has characteristic FT-IR peaks at 1740, 1655, 1590, 1507, and 1467 cm$^{-1}$.

According to another further aspect of the invention, there is provided a crystalline Form G of topotecan hydrochloride having an XRPD pattern with characteristic peaks at 6.2, 8.1, 21.2, 23.4, 25.5, 26.3, and 28.0° 2θ (±0.2°). Preferably, crystalline Form G of topotecan hydrochloride has characteristic FT-IR peaks at 1745, 1657, 1597, and 1507 cm$^{-1}$.

According to yet another further aspect of the invention, there is provided a crystalline Form H of topotecan hydrochloride having an XRPD pattern with characteristic peaks at 6.6, 10.2, 18.7, 20.5, 25.9, and 29.2° 2θ (±0.2°). Preferably, crystalline Form H of topotecan hydrochloride has characteristic FT-IR peaks at 1756, 1657, 1613, and 1537 cm$^{-1}$.

According to yet another aspect of the invention there is provided a crystalline Form I of topotecan hydrochloride having an XRPD pattern with characteristic peaks at 7.0, 10.2, 20.8, 22.1, and 27.9° 2θ (±0.2°). Preferably, crystalline Form I of topotecan hydrochloride has characteristic FT-IR peaks at 1746, 1656, 1608, 1535, and 1495 cm$^{-1}$.

According to yet another aspect of the invention there is provided a crystalline Form J of topotecan hydrochloride having an XRPD pattern with characteristic peaks at 7.8, 10.0, 16.4, 17.0, 20.2, and 27.1° 2θ (±0.2°). Preferably, crystalline Form J of topotecan hydrochloride has characteristic FT-IR peaks at 1745, 1657, 1598, and 1508 cm$^{-1}$.

According to further aspect of the invention there is provided a crystalline Form K of topotecan hydrochloride having an XRPD pattern with characteristic peaks at 6.0, 14.1, 22.8, 25.9, and 30.0° 2θ (±0.2°). Preferably, crystalline Form K of topotecan hydrochloride has characteristic FT-IR peaks at 1753, 1653, 1584, 1567, and 1512 cm$^{-1}$.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Further, the crystalline forms in accordance with some aspects of the present application have been characterized by their water content, chloride content, and solvent residue.

| Form | Water Content (wt %) | Cl Content (wt %) | Solvent residue by NMR |
|---|---|---|---|
| D | 9.73<br>9.96<br>9.50<br>(3 samples) | 9.61<br>9.76<br>9.44<br>(3 samples) | Ethanol = Not detected<br>Ethyl Acetate = 0.73% |
| E | 3.86<br>1.46<br>4.13<br>(3 samples) | 7.8<br>8.16<br>(2 samples) | Ethyl Acetate = 0.41% |
| F | 18.31 | 7.7 | Acetonitrile = 1.93% |
| G | 9.37 | 7.7 | Methanol = 1.24%<br>Ethyl Acetate = 4.57% |
| H | 2.91 | — | Methanol = 3.59%<br>Acetonitrile = 0.27% |
| I | 4.50 | — | Methanol = 0.10%<br>Acetonitrile = 4.06%<br>Ethyl Acetate = 0.31% |
| J | — | — | Methanol = 0.16%<br>Acetonitrile = 3.17%<br>Ethyl Acetate = 2.68% |

"—" means the experiment is not preformed on the crystalline form.

It is easier to remove solvents from Forms D and E than from Forms F to J by drying. In addition, the water/Cl content of Form D is more stable than that of Form E.

The stabilities of some of the crystalline forms have been tested under various conditions. HPLC was used to determine the degree of degradation of topotecan hydrochloride over time.

The samples with different forms were held at room temperature for a specific period. We tested the purities of these samples by HPLC and observed the changes of their purities.

The changes to the purities of Forms D to I are summarized as follows:

(a) The change of the purity of Form D:

| Duration Time | Purity |
|---|---|
| 0 hour | 99.32% |
| 3 days | 99.21% |
| 7 days | 99.17% |
| 20 days | 99.08% |
| 36 days | 99.43% |

(b) The change of the purity of Form E:

| Duration Time | Purity |
|---|---|
| 0 hour | 98.99% |
| 3 days | 99.27% |
| 7 days | 99.31% |
| 20 days | 99.29% |
| 36 days | 99.30% |

(c) The change of the purity of Form F:

| Duration Time | Purity |
|---|---|
| 0 hour | 99.94% |
| 3 days | 99.92% |
| 16 days | 99.91% |
| 32 days | 99.91% |

(d) The change of the purity of Form G:

| Duration Time | Purity |
|---|---|
| 0 hour | 99.11% |
| 3 days | 99.06% |
| 7 days | 99.00% |
| 20 days | 98.88% |
| 32 Days | 99.06% |

(e) The change of the purity of Form H:

| Duration Time | Purity |
|---|---|
| 0 hour | 99.92% |
| 3 days | 99.90% |
| 7 days | 99.92% |
| 20 days | 99.89% |

(f) The change of the purity of Form I:

| Duration Time | Purity |
|---|---|
| 0 hour | 99.70% |
| 3 days | 99.65% |
| 7 days | 99.56% |
| 20 days | 99.56% |

The results based on HPLC peak retention times indicate that topotecan hydrochloride in crystalline Forms D to G is substantially stable over thirty days at room temperature. And topotecan hydrochloride in crystalline Forms H and I is substantially stable over twenty days at room temperature.

According to the above-mentioned information, the water and chloride content of Form D is more stable than that of Form E, and the solvent residue of Form D is lower than that of Forms F to J. In addition, the stability of Form D at room temperature is also better than other Forms.

Form D was compared with Form A in the following two experiments.

Experiment 1

Topotecan hydrochloride (1.75 g), 99.5% ethanol (about 12 ml), the different equivalents of water {(1)3.3, (2)4.3, (3)4.5, (4)4.7, (5)4.8, (6)5.1 ml}, and the different equivalents of 2N HCl solution {(1)1.91, (2)0.96, (3)0.76, (4)0.57, (5)0.48, (6)0.19 ml} are mixed in a suitable reactor. The mixture is then heat up to about 50° C. to dissolve. Ethyl acetate (about 38 ml) is added and then cools down to about 10° C. and stir at this temperature for not less than (NLT) 1 hour. The solids are filtered and washed with cool ethyl acetate. Dry under vacuum at room temperature.

Experiment 2

Topotecan hydrochloride (4.0 g Form A or Form D) is stirred in ethyl acetate (40 mL) for a long time (40, 80, or 200 hours) at room temperature. The solids are filtered and washed with cool ethyl acetate. Dry under vacuum at room temperature.

The results of the two experiments are summarized as follows:

| Experiment No. | Results | Water Content (wt %) | Cl Content (wt %) |
|---|---|---|---|
| 1 | (1) 1.0 eq HCl$_{(aq)}$ (pH = 0.47): Form D | 9.96 | 9.76 |
|   | (2) 0.5 eq HCl$_{(aq)}$ (pH = 0.9): Form D | 9.73 | 9.61 |
|   | (3) 0.4 eq HCl$_{(aq)}$ (pH = 1.17): Form D | — | — |
|   | (4) 0.3 eq HCl$_{(aq)}$ (pH = 1.27): Form A | 11.61 | 7.69 |
|   | (5) 0.25 eq HCl$_{(aq)}$ (pH = 1.51): Form A | 16.62 | 7.74 |
|   | (6) 0.1 eq HCl$_{(aq)}$ (pH = 2-3): Form A | 10.84 | 7.60 |
| 2 | (1) 40 h: From A → A; Form D → D | — | — |
|   | (2) 80 h: Form A → E; Form D → D | | |
|   | (3) 200 h: Form A → E; Form D → D | | |

"—" means the water/Cl content test is not preformed on the sample.

According to the results of the above two experiments, Form D will be formed in the lower pH condition, and Form A will be formed in the higher pH condition. The water content of Form D is more stable than that of Form A under the different pH conditions for crystallizing.

Furthermore, Form D is more stable than Form A for a long time stirring before crystallizing. After stirring in ethyl acetate over 80 hours, Form A will transform to Form E. However, Form D will be stable even when being stirred in ethyl acetate over 200 hours.

The appearance, HCl content, and the capability of removing solvents by drying of Forms A and D are listed as follows:

| Item | Form A | Form D |
|---|---|---|
| Appearance | light yellow to Yellow | Orange |
| Equivalent HCl content | 1 | 1.4 |
| To remove solvents by drying | hard | Easy |

The HCl content of Form D is higher than that of Form A, and the solvent residue of Form D is lower than that of Form A after drying.

The following examples are provided to illustrate the process of the polymorphs of topotecan hydrochloride in accordance with the present application.

EXAMPLE 1

Water (7.5 kg) and acetonitrile (2.4 kg) were charged into a suitable reactor. The resulting mixture was heated to about 45° C. Topotecan HCl (1.5 kg) was added into resulting mixture at about 45° C., and then acetonitrile (about 21 kg) was added into the resulting mixture. After the addition was completed, the mixture was cooled to about 10° C., stirred for not less than 30 minutes, and then filtered. The wet cake was then washed with acetone (about 9 kg). The wet solids were dried under vacuum to give about 1.3 kg of Topotecan HCl Form B.

EXAMPLE 2

Topotecan HCl (1.5 kg), ethanol (about 8 kg) and water (about 4 kg) were charged into a suitable reactor. The resulting slurry was heated to about 50° C., and then filtered through silica gel and celite bed. The hot (about 50° C.) mixture of ethanol-water (Volume ratio: 7:3, about 2.5 kg) and ethyl acetate (about 5 kg) were added for rinse, and then cooled to about 35° C. Ethyl acetate (about 23 kg) was added into the resulting mixture. After the addition was completed, the mixture was cooled to about 10° C., stirred, and then filtered. The wet cake was then washed with cold Acetone (about 9 kg). The wet solids were dried under vacuum to give about 0.8 kg of Topotecan HCl Form C.

EXAMPLE 3

Topotecan HCl (1.75 g), ethanol (about 12 ml), and water (about 5 ml) were charged into a suitable reactor. The resulting slurry was heated to about 50° C. When the mixture become to a clear solution, the solution was cooled down to about 40° C. and adjusted the pH value to <1.2 with 2N HCl (aq). Ethyl acetate (about 18 ml) was added. After the addition was finished, the mixture was cooled to about 10° C. and stirred for one hour. The solids were filtered and washed with cold acetone (about 14 ml). The solids were dried under vacuum to give about 1.5 g of Topotecan HCl Form D.

EXAMPLE 4

Crystallization

Water (about 8 kg) and acetonitrile (about 2 kg) were charged into a suitable reactor. The resulting mixture was heated to about 40° C. Topotecan HCl (about 1.5 kg) was added into the resulting mixture, and then acetonitrile (about 21 kg) was added into the resulting mixture. After the addition was completed, the mixture was cooled to below 10° C., and then filtered. The wet cake was then washed with acetone (about 9 kg). The wet solids were dried to give about 1.3 kg of topotecan HCl.

Re-Crystallization

Ethanol (about 8 kg) and water (about 4 kg) were charged into a suitable reactor and heated to 35-50° C., and then topotecan HCl obtained from the crystallization of example 3 (about 1.0 kg) was added into the resulting mixture (Add HCl aqueous solution if pH is greater than 1.2.), and then filtered through a silica gel and celite bed. A mixture of ethanol/water (volume ratio: 7:3, about 2.5 kg) and ethyl acetate (about 5 kg) was added for rinse and then cooled to 30-45° C. Ethyl acetate (about 23 kg) was added into the resulting mixture. After the addition was completed, the mixture was cooled to below 10° C., and then filtered. The wet cake was then washed with ethyl acetate (about 11 kg). The wet solids were dried to give 0.7-0.9 kg of topotecan HCl Form D.

Two samples of topotecan HCl Form D produced by Example 4 were analyzed to identify their impurity content, water content and Cl content. The results are summarized as follows:

|  | Sample No. | |
| --- | --- | --- |
|  | 1 | 2 |
| Total impurities by HPLC | 0.09% | 0.09% |
| Water Content: Karl Fischer (wt %) | 9 | 8 |
| Chloride Content: Titration (wt %) | 9.8 | 9.6 |

EXAMPLE 5

Crystallization

Topotecan hydrochloride (1 g) was suspended in 15 mL of N,N-Dimethylformamide and heated up to 50° C. to give off-white slurry. It had been stirring for 10 min, and then 40 mL of ethyl acetate were added. The mixture was stirred under reflux for more 15 min, then cooled down to room temperature in 30 min. The precipitate was filtered and dried to give about 0.5 g of topotecan HCl.

Re-Crystallization

Ethanol (about 4 g) and water (about 2 g) were charged into a suitable reactor and heated to 35-50° C., and then topotecan HCl obtained from the crystallization of example 4 (about 0.5 g) was added into the resulting mixture (Add HCl aqueous solution if pH is greater than 1.2.), and then filtered through a silica gel and celite bed. A mixture of ethanol/water (volume ratio: 7:3, about 1.2 g) and ethyl acetate (about 2.5 g) was added for rinse and then cooled to 30-45° C. Ethyl acetate (about 11.5 g) was added into the resulting mixture. After the addition was completed, the mixture was cooled to below 10° C., and then filtered. The wet cake was then washed with ethyl acetate (about 5.5 g). The wet solids were dried to give 0.35-0.45 g of topotecan HCl Form D.

EXAMPLE 6

Topotecan HCl (8.0 g), and about 0.04% HCl in Ethyl acetate (about 240 ml) were charged into a suitable reactor. The resulting slurry was stirred for not less than 80 hours. The solids were filtered and washed with Ethyl acetate (80 ml). The solids were dried under vacuum to give about 7 g of Topotecan HCl Form E.

EXAMPLE 7

Topotecan HCl (about 1.6 g) and water (about 10 ml) were charged into a suitable reactor to form thick slurry, and acetonitrile (about 3 ml) was added. The resulting slurry was heated to 30-40° C. Adjusted the pH value to 2 by 2N $HCl_{(aq)}$. Then the slurry was heated to about 45° C. When the solids were dissolved, acetonitrile (about 30 ml) was added. The slurry was cooled to about 10° C. and stirred for 1 hour. The solids were filtered and washed with cold acetonitrile (about 8 ml). The solids were dried under vacuum to give about 1.5 g of Topotecan HCl Form F.

EXAMPLE 8

Topotecan HCl (2.0 g), Methanol (about 16 ml), and Water (about 4 ml) were charged into a suitable reactor. The resulting slurry was heated to about 50° C. When the solids were dissolved, ethyl acetate (about 36 ml) was added at room temperature. The slurry was cooled to about 10° C. and stirred for 1 hour. The solids were filtered and washed with cold ethyl acetate (about 10 ml). The solids are dried under vacuum to give about 1 g of Topotecan HCl Form G.

EXAMPLE 9

Topotecan HCl (about 1 g), 3% $HCl_{(g)}$ in Methanol (about 22 ml), and acetonitrile (about 16 ml) were charged into a suitable reactor. The slurry was heated to about 50° C. and kept for 1 hour. Then the slurry was cooled to about 10° C. and stirred for 1 hour. The solids were filtered and washed with cold ethyl acetate (about 10 ml). The solids were dried under vacuum to give about 0.8 g of Topotecan HCl Form H.

EXAMPLE 10

Topotecan HCl (about 1.7 g), 1% $HCl_{(g)}$ in Methanol (about 34 ml), and acetonitrile (about 25 ml) were charged into a suitable reactor. The slurry was heated to about 50° C. and ethyl acetate (about 67 ml) was added. The slurry was cooled to about 10° C. and stirred for 1 hour. The solids were filtered and washed with cold ethyl acetate (about 10 ml). The solids were dried under vacuum to give about 1.5 g of Topotecan HCl Form I.

EXAMPLE 11

Topotecan HCl (about 2.0 g), Methanol (about 40 ml), and acetonitrile (about 30 ml) were charged into a suitable reactor. The slurry was heated to about 50° C. and then stirred for over 30 minutes. The slurry was cooled to about 10° C. and stirred for 1 hour. The solids were filtered and washed with cold ethyl acetate (about 20 ml). The solids were dried under vacuum to give about 1.8 g of Topotecan HCl Form J.

EXAMPLE 12

Topotecan HCl (about 20 g) and about 0.04% HCl in Ethyl acetate (about 600 ml) were charged into a suitable reactor.

The resulting slurry was stirred for about 30 hours. The solids were filtered and washed with Ethyl acetate (about 100 ml). The solids were dried under vacuum to give about 17.6 g of Topotecan HCl Form K.

Furthermore, crystallization/re-crystallization can also remove the impurities produced from the manufacturing process of topotecan HCl. When the impurities contained in the crude topotecan HCl cannot be removed by crystallizing at a time, re-crystallization can be conducted on the topotecan HCl. The crystalline form of the final topotecan HCl will be certain until the last time crystallization.

Therefore, the above-mentioned examples and any combination thereof can be conducted on topotecan HCl to remove impurities contained in topotecan HCl. Especially, one identified impurity, 9-hydroxymethyl-10-hydroxy-camptothecin (MW=394), which may formed during the manufacturing process of topotecan HCl and the purification process where water is present, can be removed efficiently by the processes in example 4 and 5. The 9-hydroxymethyl-10-hydroxy-camptothecin can be removed by the crystallization, and then the re-crystallization can control the target crystalline form of topotecan HCl.

Crystallizing crude topotecan HCl via dissolving it in high polar solvent system (more polar than the anti-solvent), and precipitating it after adding the low polar anti-solvent can efficiently remove 9-hydroxymethyl-10-hydroxy-camptothecin from it.

The impurity of the final topotecan hydrochloride is preferably less than 0.10% based on the total weight of the final topotecan hydrochloride.

The invention is not limited by the embodiments described above which are presented as examples only but can be modified in various ways within the scope of protection defined by the appended patent claims.

We claim:

1. A crystalline Form D of topotecan hydrochloride having powder X-ray diffraction peaks at 5.9, 13.9, 22.6, 23.2, and 26.5° 2θ (±0.2°).

2. The crystalline Form D of claim 1 having infrared diffuse-reflectance peaks at approximately 1742, 1654, 1586, 1510, and 1467 cm$^{-1}$.

Figure 4:
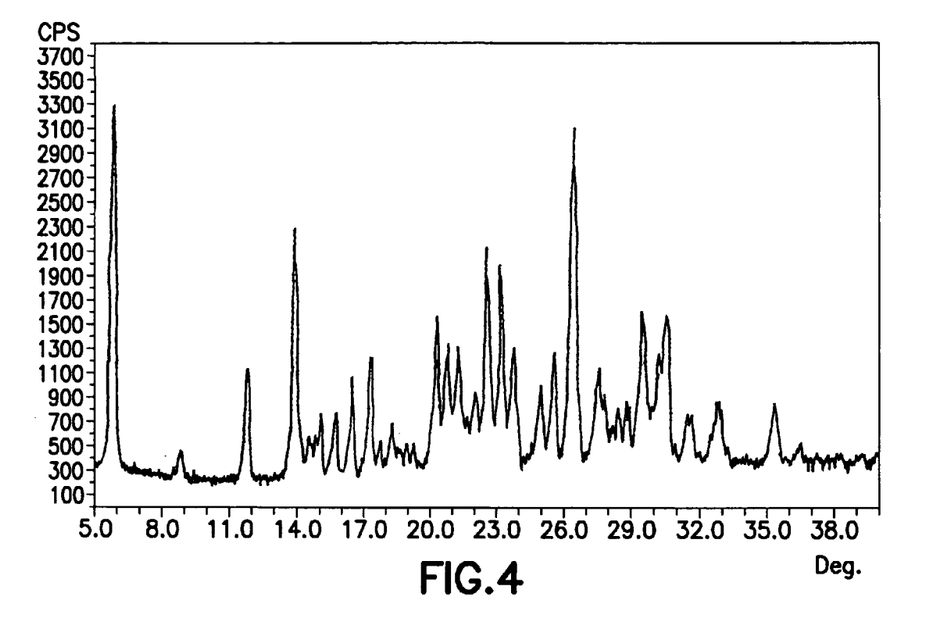
FIG. 4 is a characteristic powder X-ray diffraction pattern of Form D.

3. The crystalline Form D claim 1 having substantially the same X-ray diffraction pattern as shown in FIG. 4.

Figure 5:
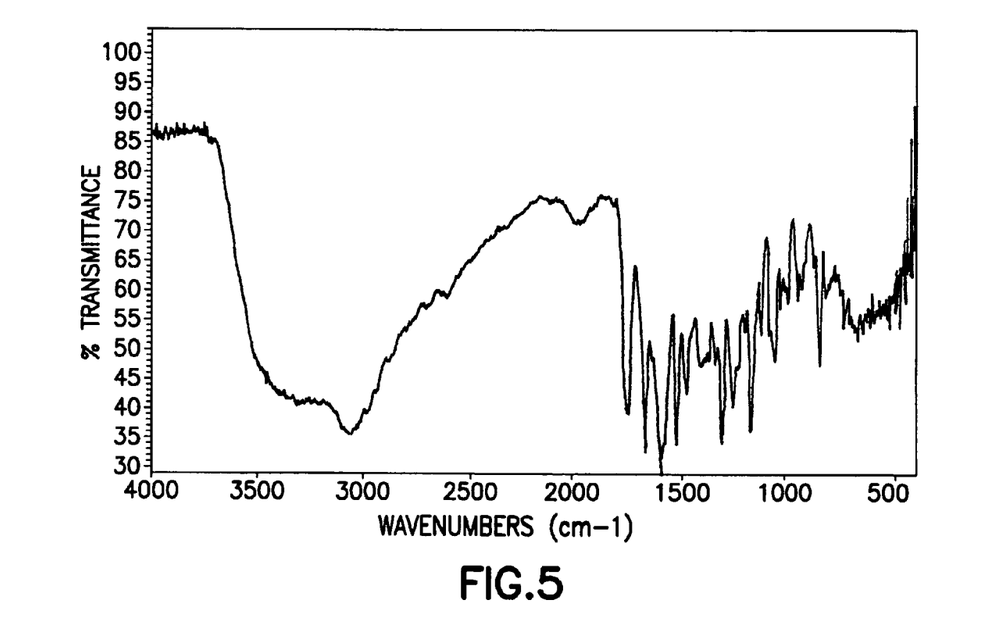
FIG. 5 is an infrared diffuse reflectance pattern of Form D.

4. The crystalline Form D of claim 1 having substantially the same infrared diffuse-reflectance pattern as shown in FIG. 5.

5. The crystalline Form D of claim 1 wherein the water content of Form D is 7 to 11 wt %.

6. The crystalline Form D of claim 1, wherein the chloride content of Form D is 8.5 to 10.5 wt %.

7. A crystalline Form E of topotecan hydrochloride having powder X-ray diffraction peaks at 14.0, 18.8, 22.5, 25.4, and 25.7° 2θ (±0.2°).

8. The crystalline Form E of claim 7 having infrared diffuse-reflectance peaks at approximately 1752, 1649, 1584, 1567, and 1513 cm$^{-1}$.

Figure 6:
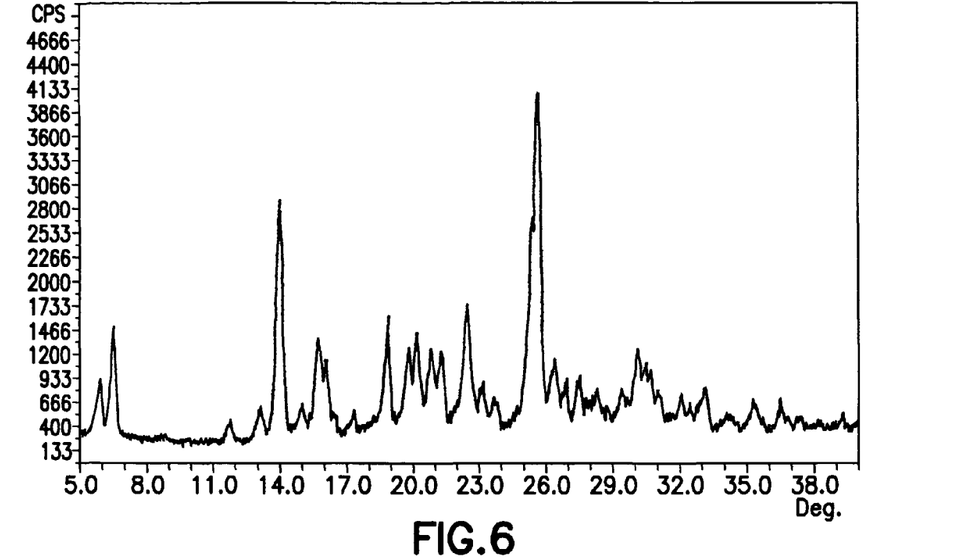
FIG. 6 is a characteristic powder X-ray diffraction pattern of Form E.

9. The crystalline Form E of claim 7 having substantially the same X-ray diffraction pattern as shown in FIG. 6.

Figure 7:
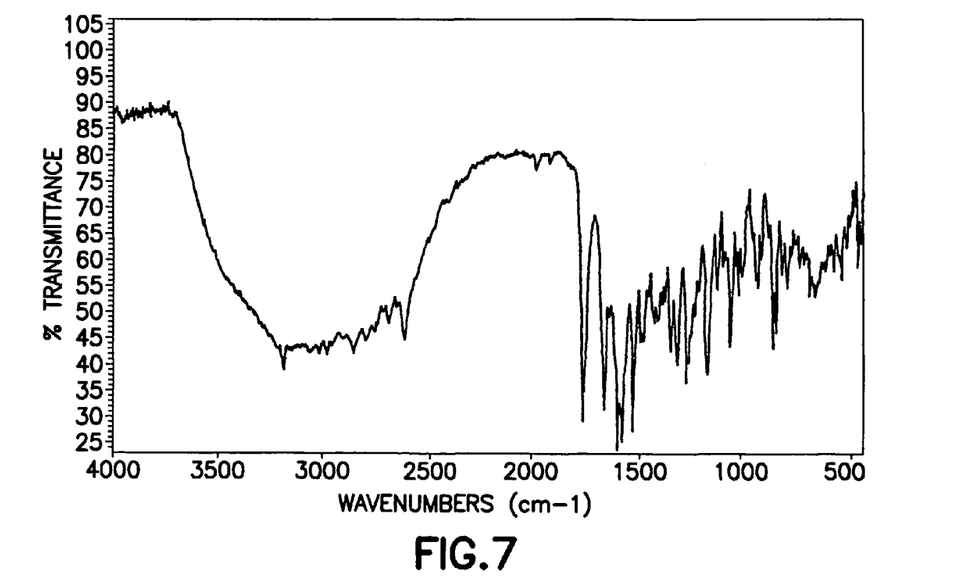
FIG. 7 is an infrared diffuse reflectance pattern of Form E.
Figure 8:
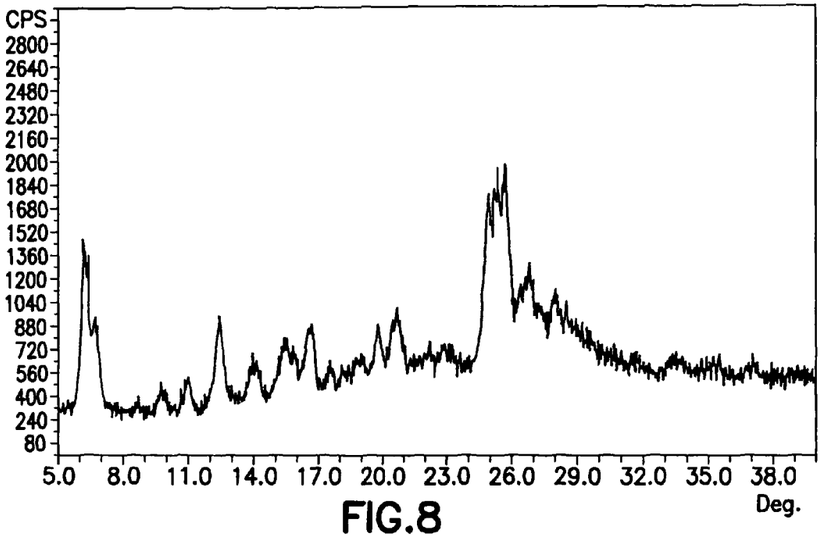
FIG. 8 is a characteristic powder X-ray diffraction pattern of Form F.
Figure 9:
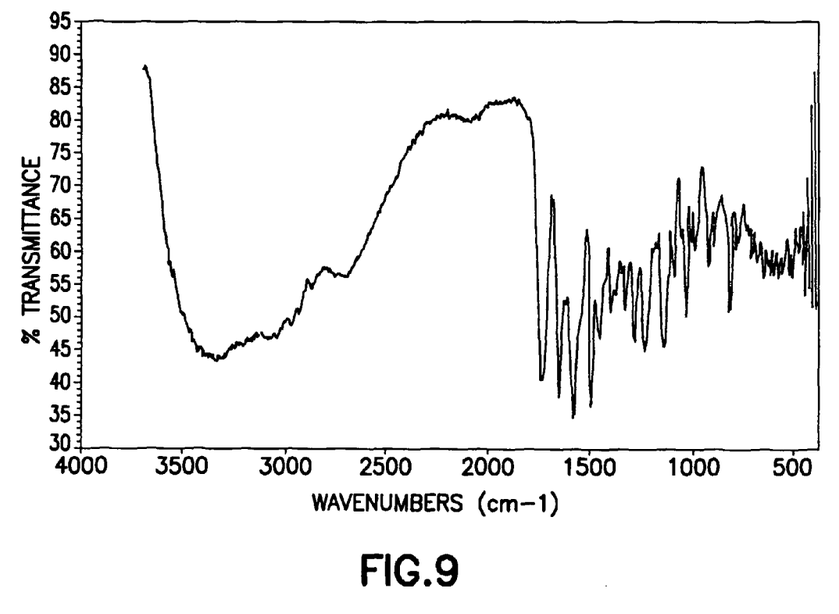
FIG. 9 is an infrared diffuse reflectance pattern of Form F.
Figure 10:
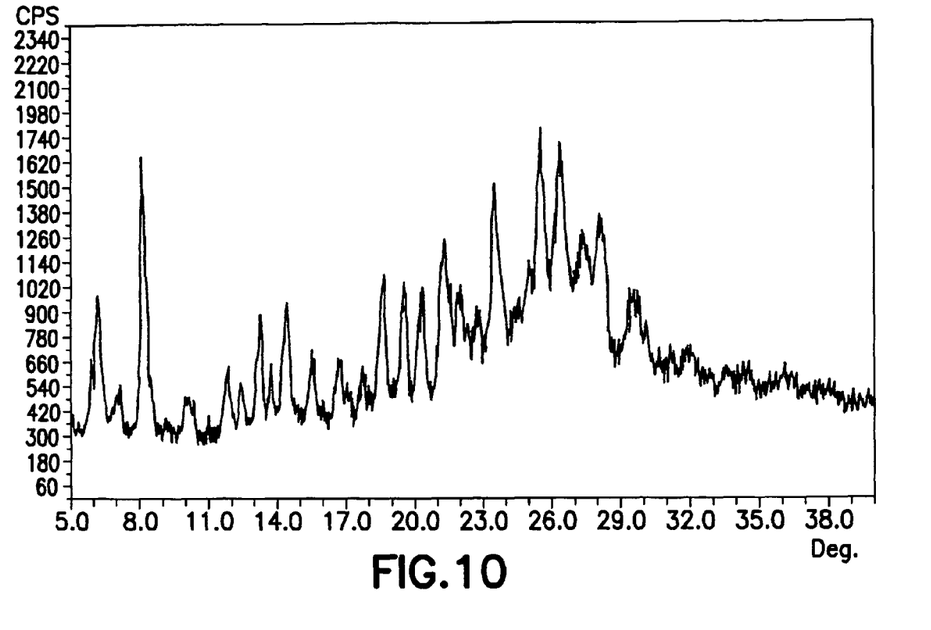
FIG. 10 is a characteristic powder X-ray diffraction pattern of Form G.
Figure 11:
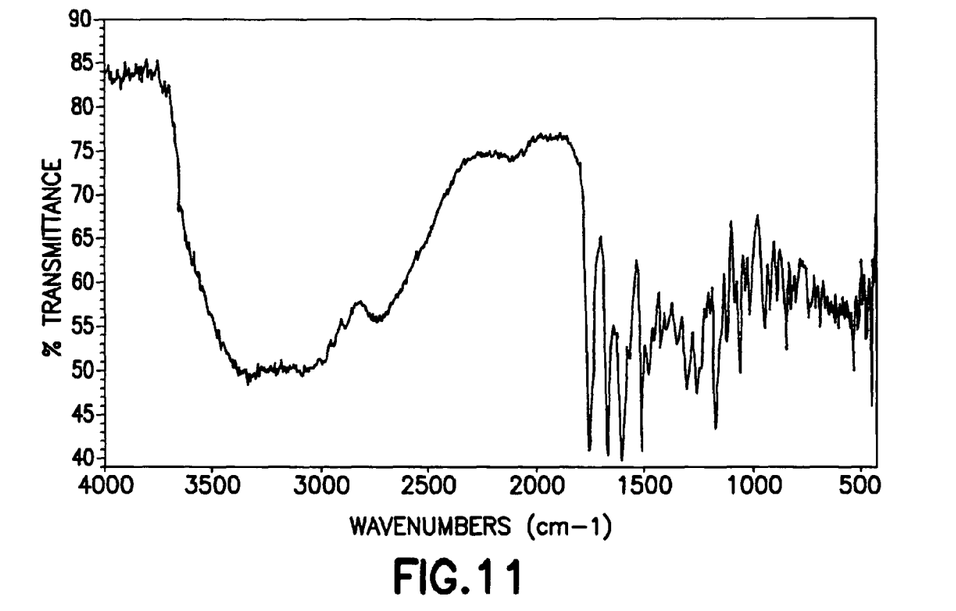
FIG. 11 is an infrared diffuse reflectance pattern of Form G.
Figure 12:
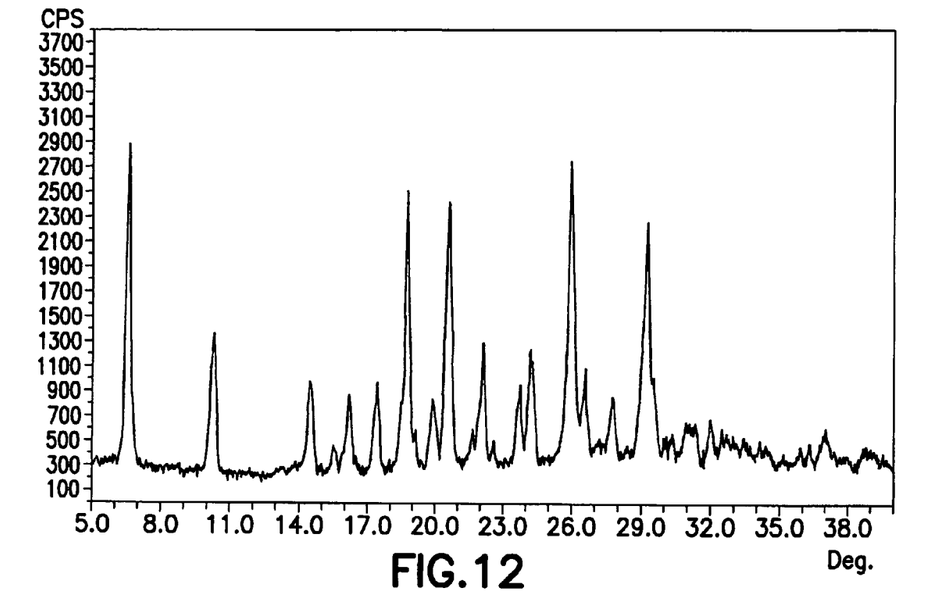
FIG. 12 is a characteristic powder X-ray diffraction pattern of Form H.
Figure 13:
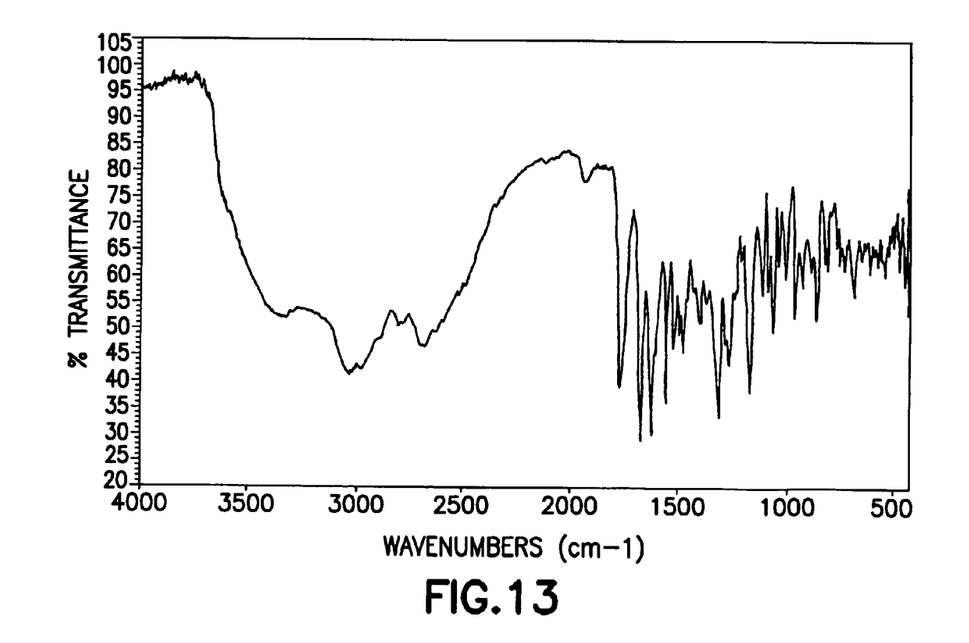
FIG. 13 is an infrared diffuse reflectance pattern of Form H.
Figure 14:
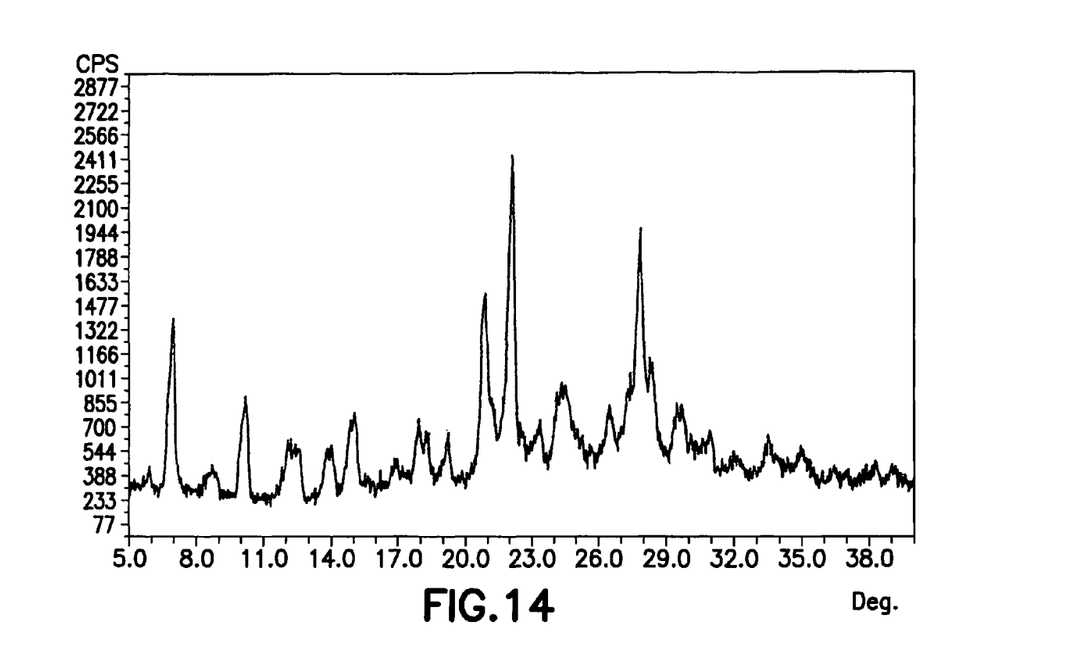
FIG. 14 is a characteristic powder X-ray diffraction pattern of Form I.
Figure 15:
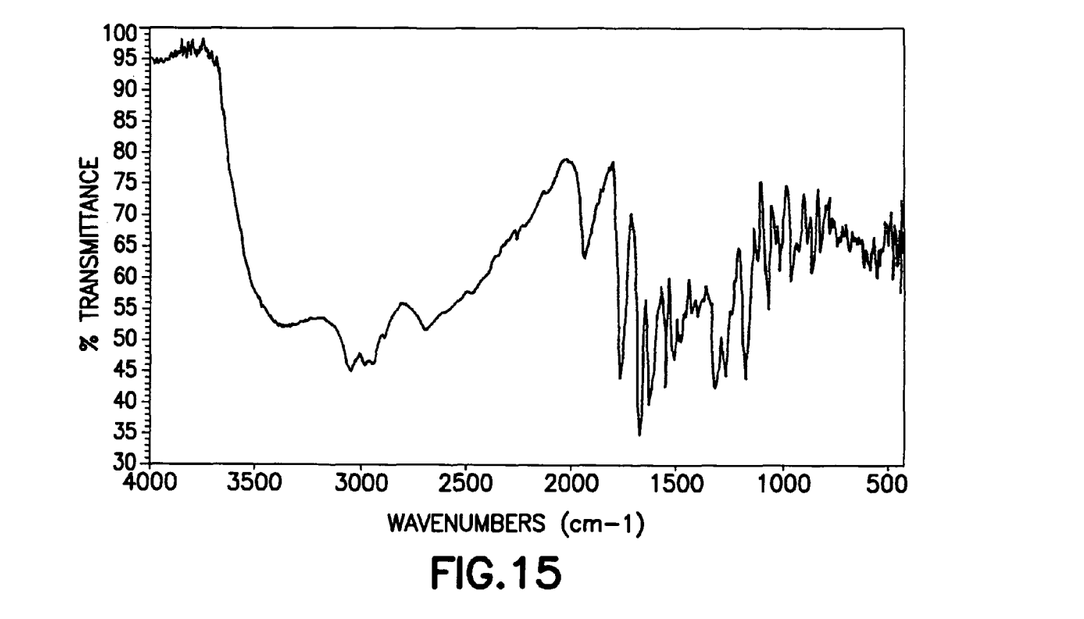
FIG. 15 is an infrared diffuse reflectance pattern of Form I.
Figure 16:
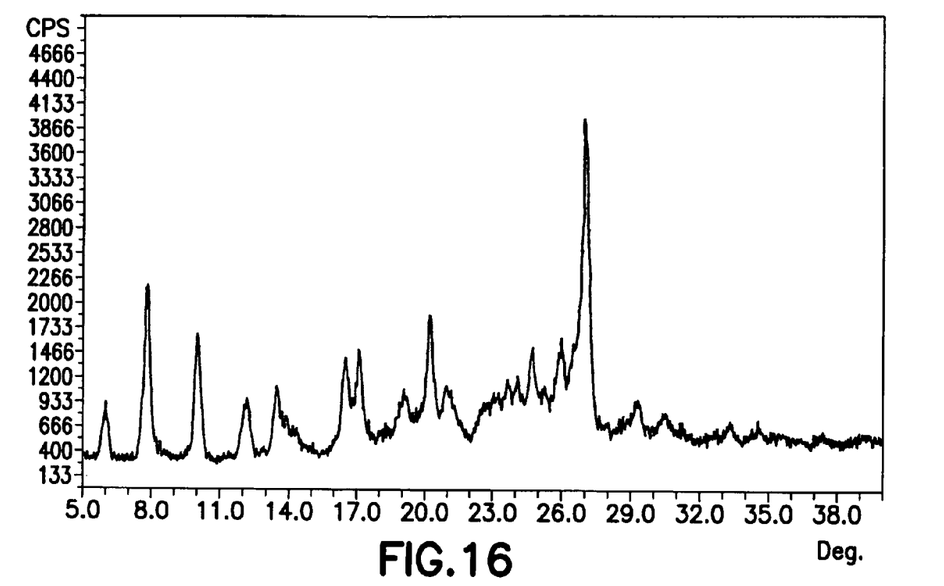
FIG. 16 is a characteristic powder X-ray diffraction pattern of Form J.
Figure 17:
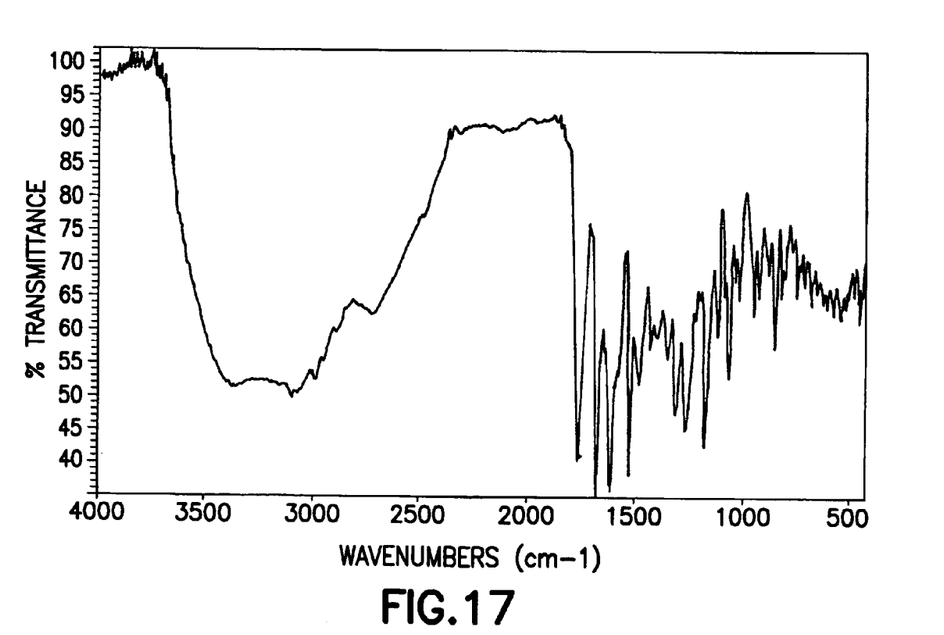
FIG. 17 is an infrared diffuse reflectance pattern of Form J.
Figure 18:
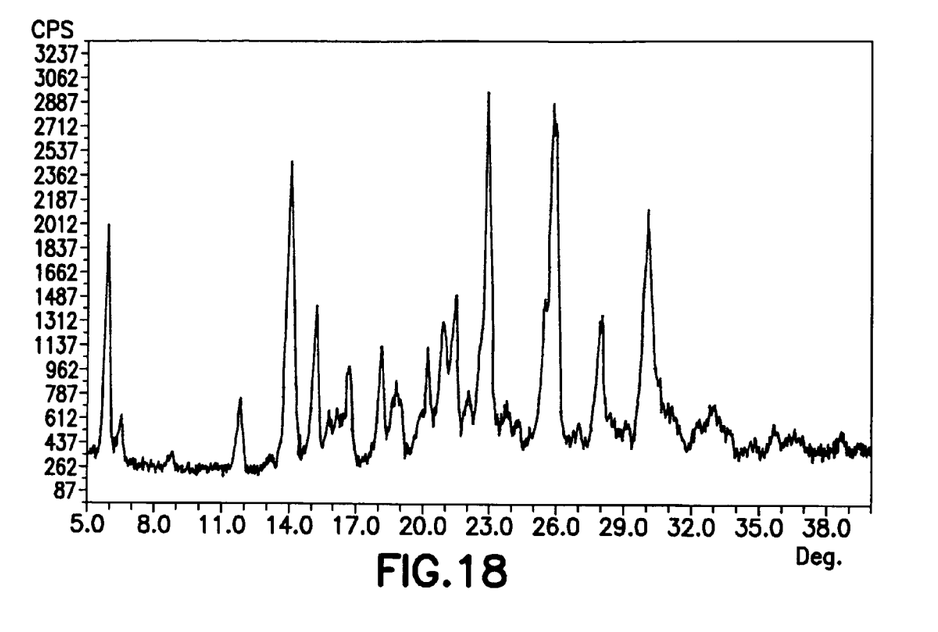
FIG. 18 is a characteristic powder X-ray diffraction pattern of Form K.
Figure 19:
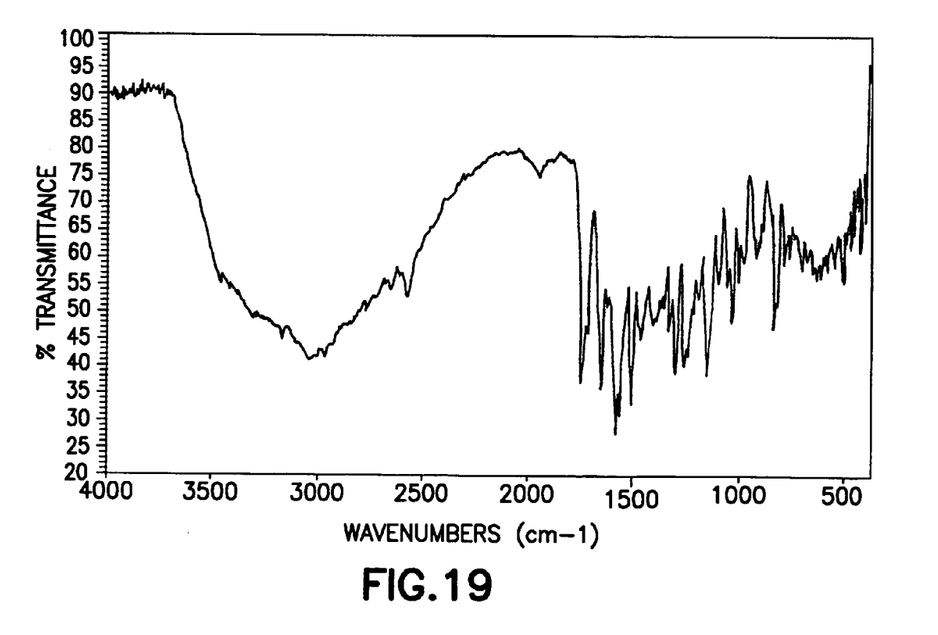
FIG. 19 is an infrared diffuse reflectance pattern of Form K.
Figure 20:
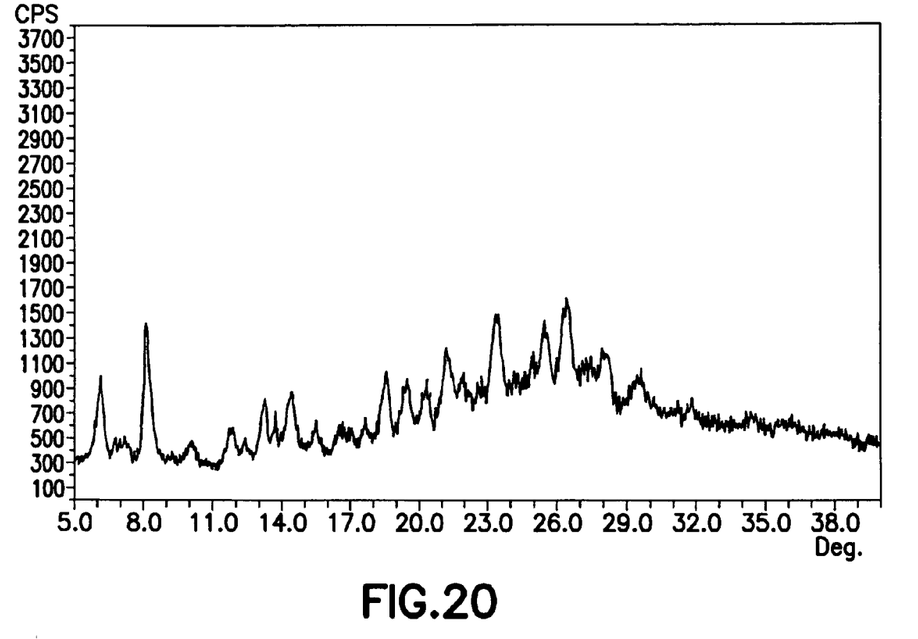
FIG. 20 is a characteristic powder X-ray diffraction pattern of Form B.

10. The crystalline Form E of claim 7 having substantially the same infrared diffuse-reflectance pattern as shown in FIG. 7.

11. A process for preparing the topotecan hydrochloride Form D of claim 1 comprising:
    (a) dissolving topotecan hydrochloride in a first solvent system;
    (b) adjusting the pH of the resulting mixture of step (a) to below 1.2;
    (c) adding a volume of low polar solvent into the mixture of step (b) to form a second solvent system, wherein the first solvent system is more polar than the second solvent system; and
    (d) crystallizing the topotecan hydrochloride Form D from the second solvent system.

12. The process of claim 11, wherein the first solvent system is a mixture of water miscible organic solvent and water.

13. The process of claim 11, wherein the water miscible organic solvent is a lower C1-C6 alcohol solvent.

* * * * *